United States Patent
Stevens et al.

(10) Patent No.: US 11,331,057 B2
(45) Date of Patent: May 17, 2022

(54) C-ARM CAP

(71) Applicant: C-Thru, Salt Lake City, UT (US)

(72) Inventors: Peter M. Stevens, Salt Lake City, UT (US); John Colin Stevens, Salt Lake City, UT (US)

(*) Notice: Subject to any disclaimer, the term of this patent is extended or adjusted under 35 U.S.C. 154(b) by 0 days.

(21) Appl. No.: 17/401,754

(22) Filed: Aug. 13, 2021

(65) Prior Publication Data
US 2022/0047230 A1    Feb. 17, 2022

Related U.S. Application Data

(60) Provisional application No. 63/088,591, filed on Oct. 7, 2020, provisional application No. 63/066,536, filed on Aug. 17, 2020.

(51) Int. Cl.
| | |
|---|---|
| A61B 6/10 | (2006.01) |
| A61B 46/10 | (2016.01) |
| A61B 6/00 | (2006.01) |
| A61B 50/00 | (2016.01) |

(52) U.S. Cl.
CPC .............. *A61B 6/10* (2013.01); *A61B 6/4225* (2013.01); *A61B 6/4441* (2013.01); *A61B 46/10* (2016.02); *A61B 2050/006* (2016.02); *A61B 2050/0067* (2016.02); *A61B 2050/0083* (2016.02)

(58) Field of Classification Search
CPC ....... A61B 6/10; A61B 6/4225; A61B 6/4441; A61B 46/10; A61B 2050/006; A61B 2050/0067; A61B 2050/0083
See application file for complete search history.

(56) References Cited

U.S. PATENT DOCUMENTS

| | | | |
|---|---|---|---|
| 2,910,259 A * | 10/1959 | Johnson | A61G 13/12 248/118 |
| 3,934,140 A * | 1/1976 | Dutertre | A61B 6/04 378/179 |
| 4,688,780 A * | 8/1987 | Hanz | A61B 6/0421 5/601 |
| 4,698,837 A | 10/1987 | Van Steenburg | |
| 5,443,233 A | 8/1995 | Kabanek | |
| 5,642,541 A | 7/1997 | Corbin | |
| 5,675,851 A * | 10/1997 | Feathers | A61G 13/12 5/601 |
| 6,101,650 A | 8/2000 | Omdal et al. | |
| 6,222,906 B1 * | 4/2001 | Sakaguchi | H01L 27/14663 378/95 |
| 6,898,810 B2 * | 5/2005 | Steven | A61B 6/0442 5/601 |
| 2001/0036245 A1 * | 11/2001 | Kienzle, III | A61B 90/36 378/4 |
| 2005/0047554 A1 * | 3/2005 | Borom | A61B 6/4441 378/209 |

(Continued)

*Primary Examiner* — Dani Fox
*Assistant Examiner* — Soorena Kefayati
(74) *Attorney, Agent, or Firm* — Thorpe, North & Western, LLP

(57) ABSTRACT

A cap for a c-arm medical imaging device with an image intensifier comprises a plate sized and shaped to cover an exterior facing surface of the image intensifier. The plate is transparent to x-rays and has a planar center with a planar outer surface and a planar inner surface to face the image intensifier. A retainer is carried by the plate to retain the plate on the image intensifier.

19 Claims, 6 Drawing Sheets

(56) References Cited

U.S. PATENT DOCUMENTS

| | | | |
|---|---|---|---|
| 2005/0047734 A1* | 3/2005 | Borom | A61B 46/00 385/98 |
| 2005/0171428 A1* | 8/2005 | Fichtinger | A61B 8/12 378/190 |
| 2013/0167845 A1* | 7/2013 | Grajek | A61B 46/27 128/856 |
| 2013/0240402 A1* | 9/2013 | Campista | B32B 27/12 428/34.1 |
| 2014/0104789 A1* | 4/2014 | Zhu | H05K 7/20409 361/700 |
| 2015/0010131 A1* | 1/2015 | Arisaka | A61B 6/4488 378/197 |
| 2015/0124941 A1* | 5/2015 | Arterson | A61B 6/4441 378/204 |
| 2015/0297150 A1* | 10/2015 | Grimbergen | A61B 6/502 378/37 |
| 2015/0320370 A1* | 11/2015 | Bouvier | A61B 6/4441 378/189 |
| 2016/0231440 A1* | 8/2016 | Burke | G01T 1/2018 |
| 2019/0076104 A1* | 3/2019 | Rosink | A61B 6/06 |

\* cited by examiner

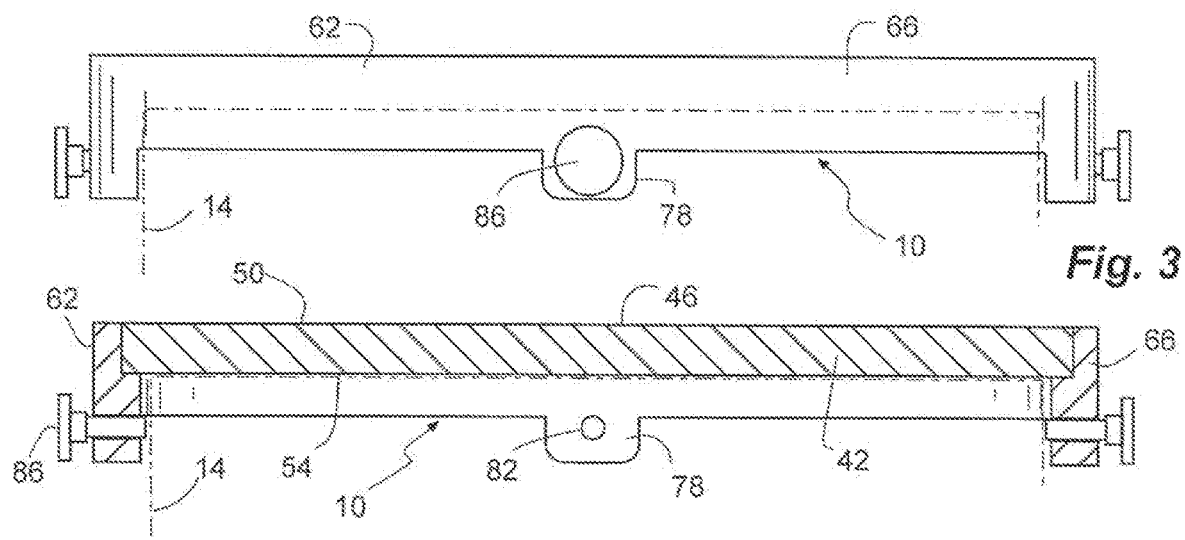
Fig. 3
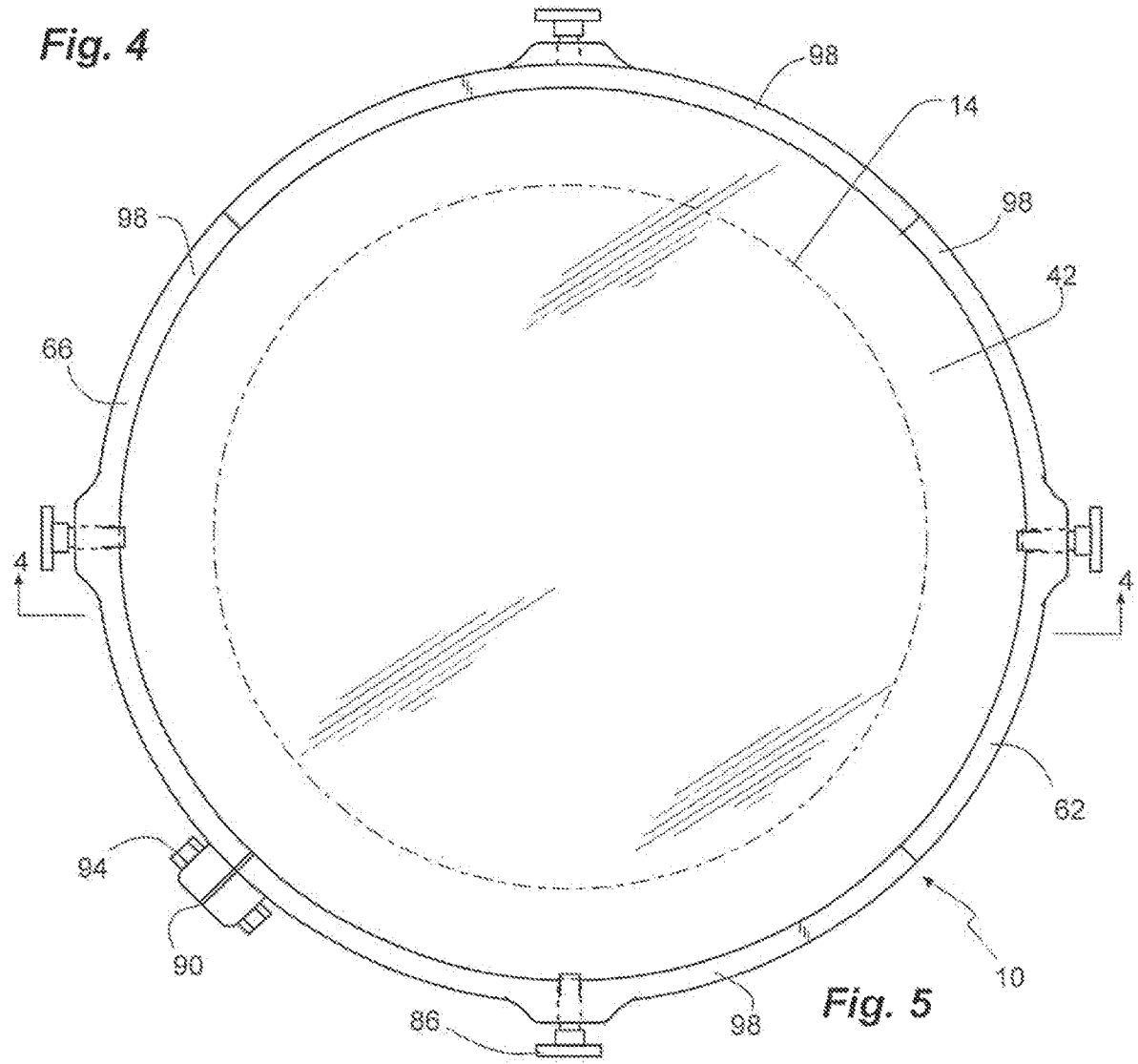
Fig. 4
Fig. 5

C-ARM CAP

PRIORITY CLAIM(S)

Priority is claimed to U.S. Provisional Patent Application Nos. 63/066,536, filed Aug. 17, 2020, and 63/088,591, filed Oct. 7, 2020, which are hereby incorporated herein by reference.

BACKGROUND

C-arm x-ray machines are medical imaging devices in which a C-shaped arm is used to connect an x-ray source and an image intensifier to one another and orient the x-ray source and the image intensifier to oppose one another. Sometimes, medical personnel utilize the image intensifier as a table and perform procedures such as surgery directly on the image intensifier. If the image intensifier is punctured during surgery, there is a risk of electrocution. In addition, the cost to repair or replace the image intensifier is significant.

BRIEF DESCRIPTION OF THE DRAWINGS

Features and advantages of the invention will be apparent from the detailed description which follows, taken in conjunction with the accompanying drawings, which together illustrate, by way of example, features of the invention; and, wherein:

FIG. 3 is a side view of the cap of FIG. 1.

FIG. 4 is a cross-sectional side view of the cap of FIG. 1.

FIG. 5 is a top view of the cap of FIG. 1.

Figure 1:
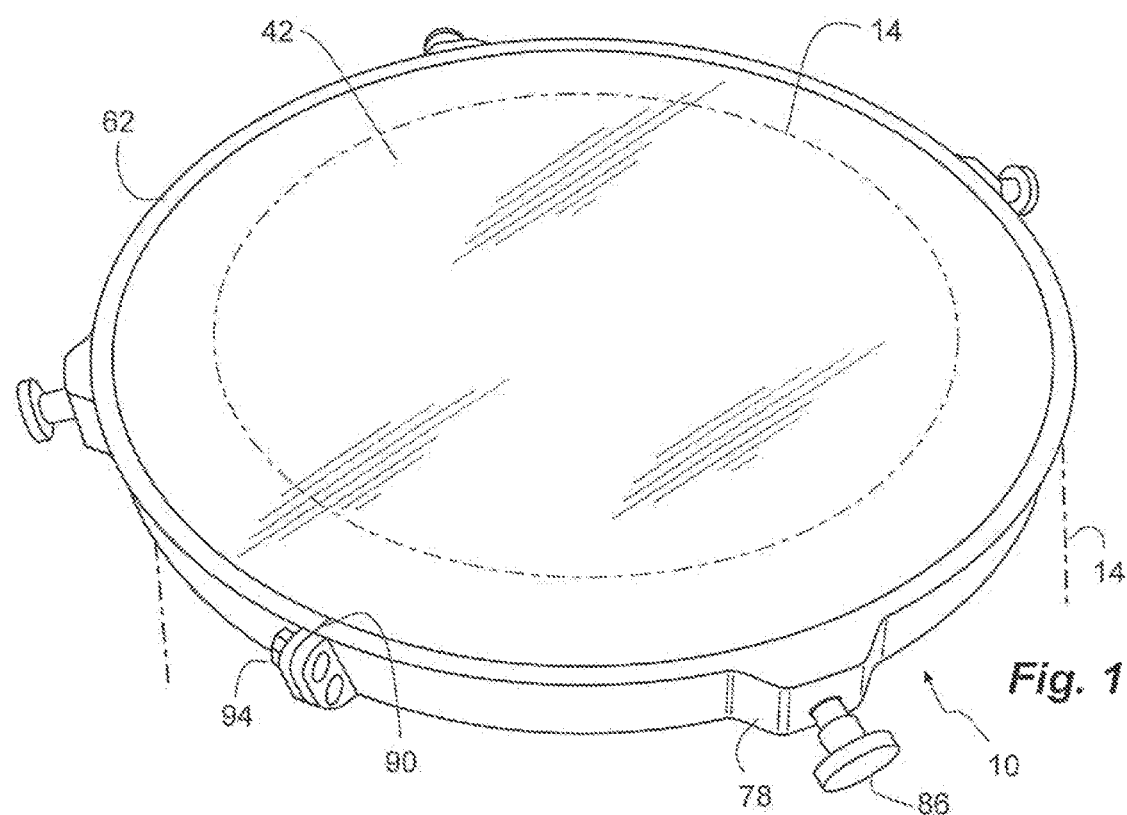
FIG. 1 is a perspective view of a cap shown covering an image intensifier of a medical imaging device in accordance with an embodiment of the invention.
Figure 2:
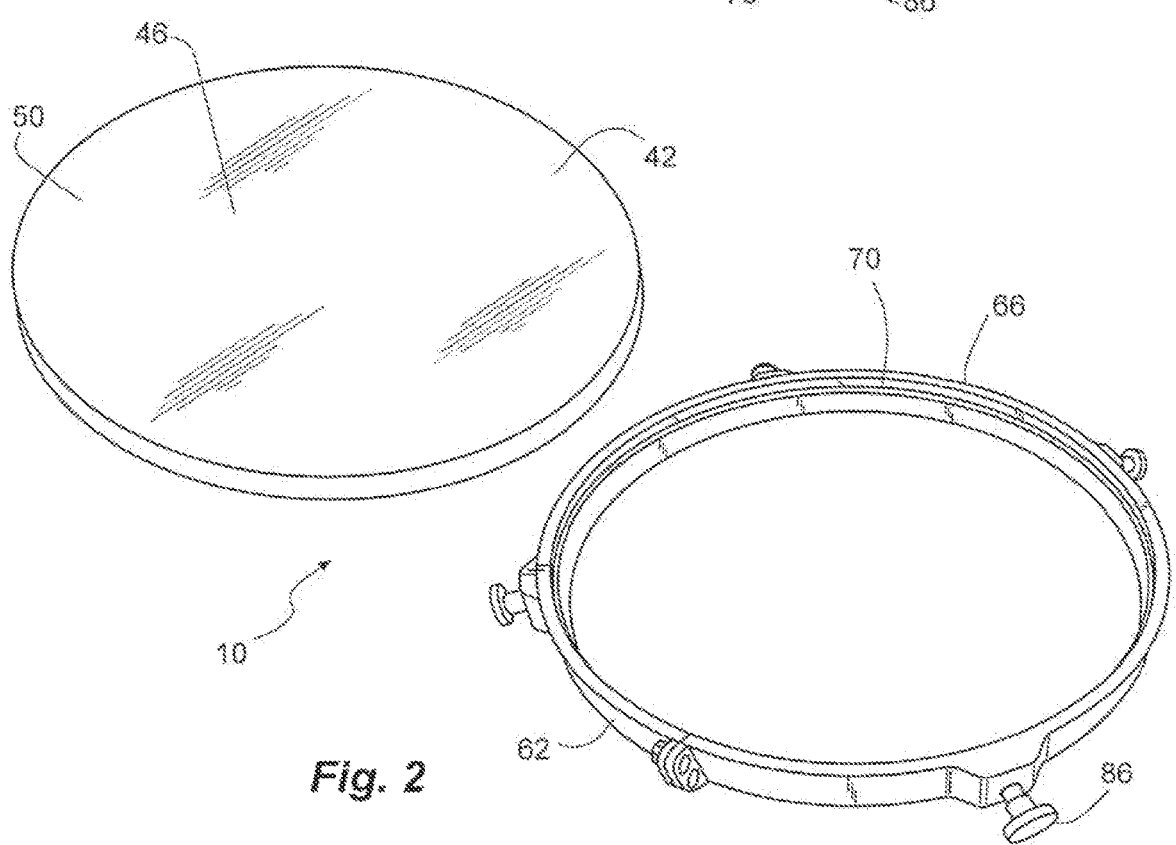
FIG. 2 is a perspective exploded view of the cap of FIG. 1.

Reference will now be made to the exemplary embodiments illustrated, and specific language will be used herein to describe the same. It will nevertheless be understood that no limitation of the scope of the invention is thereby intended.

DETAILED DESCRIPTION

Before invention embodiments are disclosed and described, it is to be understood that no limitation to the particular structures, process steps, or materials disclosed herein is intended, but also includes equivalents thereof as would be recognized by those ordinarily skilled in the relevant arts. It should also be understood that terminology employed herein is used for the purpose of describing particular examples only and is not intended to be limiting. The same reference numerals in different drawings represent the same element. Numbers provided in flow charts and processes are provided for clarity in illustrating steps and operations and do not necessarily indicate a particular order or sequence. Unless defined otherwise, ail technical and scientific terms used herein have the same meaning as commonly understood by one of ordinary skill in the art to which this disclosure belongs.

An initial overview of the inventive concepts are provided below and then specific examples are described in further detail later. This initial summary is intended to aid readers in understanding the examples more quickly, but is not intended to identify key features or essential features of the examples, nor is it intended to limit the scope of the claimed subject matter.

The invention provides a cap for a medical imaging device with an image intensifier, such as a c-arm. The cap can provide a rigid solid surface to support a patient's limb, or other medical equipment, on and/or over the image intensifier while protecting the image intensifier from damage and the patient from injury. In addition, the cap can provide a work surface while protecting the image intensifier from damage, such as by inadvertent puncture by a surgical instrument. The patient's limb and the medical procedure can be supported by and carried by the image intensifier of the c-arm with the cap, or a portion thereof, interposed between the image intensifier and the patient's limb and medical equipment and medical personnel. In addition, the cap or a portion thereof can be translucent to x-rays so that the c-arm medical imaging device can be utilized for imaging without interference from the cap.

Figure 6:
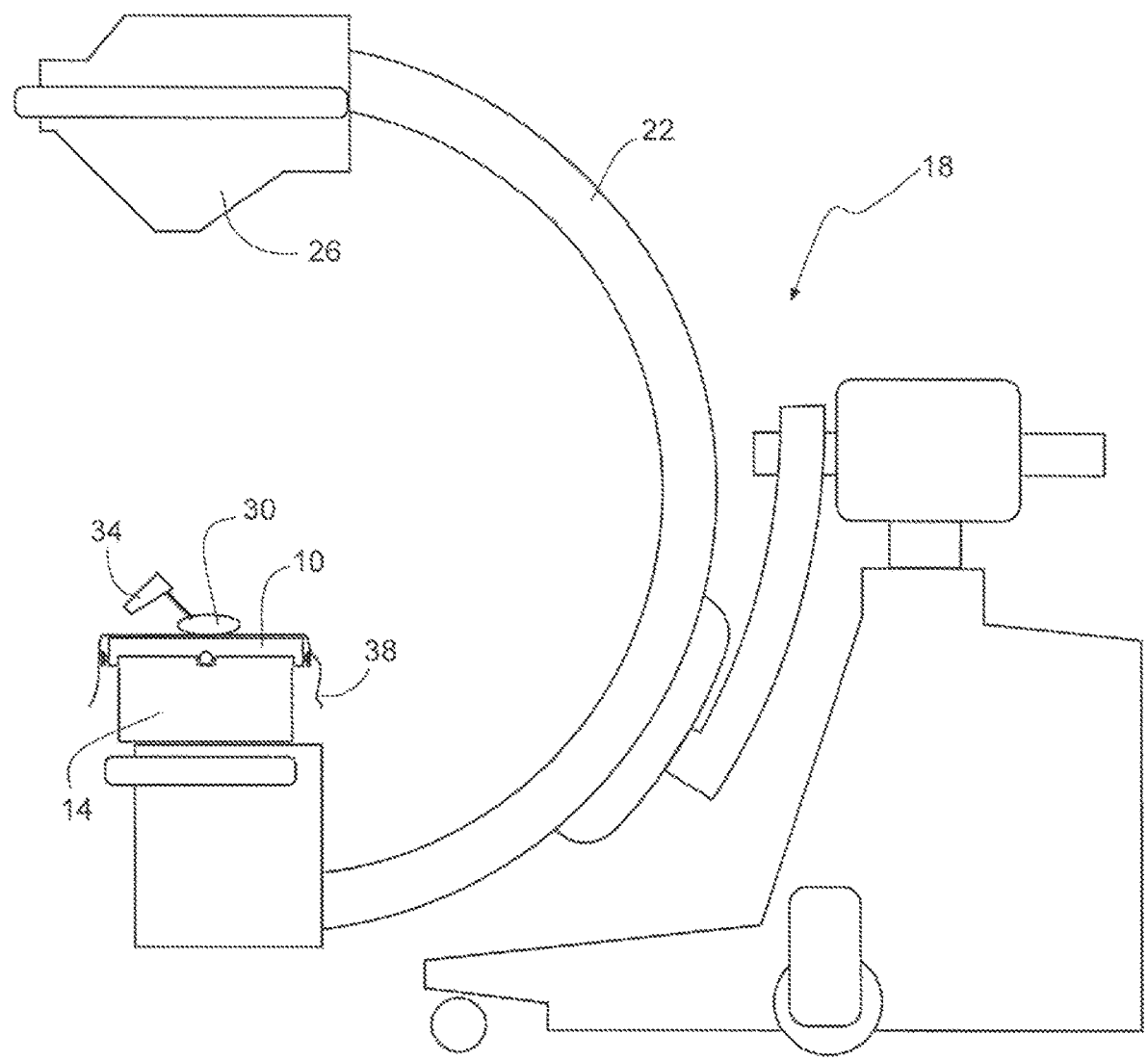
FIG. 6 is a schematic view of the cap of FIG. 1 covering the image intensifier of the c-arm medical imaging device and in use during a medical procedure in accordance with another embodiment of the invention.

Referring to FIGS. 1-6, a cap 10 is shown for protecting and/or covering an image intensifier 14 of a medical imager 18, such as a c-arm medical imaging device. The image intensifier 14 can be a camera or detector earned on one end of a c-arm 22; and an x-ray tube/source 26 can be carried on an opposite end of the c-arm 22 opposing the image intensifier 14. As described above, the c-arm 22 can be oriented with the image intensifier 14 oriented to face upward and horizontal to be utilized as a support surface for medical procedures, as shown in FIG. 6. The medical procedure can involve placing a patient's limb 30 over the image intensifier 14 with the cap 10 between the limb 30 and the image intensifier 14. In addition, the medical procedure can utilize a medical implement 34, such as a drill or scalpel that would otherwise be capable of piercing the image intensifier 14 leading to death, injury, and/or damage. The image intensifier 14 can contain expensive and dangerous electronics. The cap 10 interposed between the image intensifier 14 and the implement 34 resists the implement 34 from contacting and piercing the image intensifier 14. In addition, a drape 38 can be placed over the cap 10 and the image intensifier 14, and under the limb 30 and the implement 34. The medical procedure can further comprise imaging with the imaging system 18 while the limb 30 is on the cap 10 and the image intensifier 14.

The cap 10 can comprise a plate 42 sized and shaped to cover an exterior facing surface of the image intensifier 14. In one aspect, the cap 10 and the plate 42 can cover an entire exterior facing surface of the image intensifier 14. In another aspect, at least the plate 42 can be transparent to x-rays.

Thus, the medical imager 18 can be utilized with the cap 10 thereof. In addition, the plate 42 can have a planar center 46 with a planar outer surface 50 to receive and support the patient's limb 30. In one aspect, the plate 42 and the center 46 thereof can be flat and continuous to resist interfering with medical procedures. In another aspect, the plate 42 and the center 46 thereof can have indentations and/or protrusions to support and facilitate medical procedures. For example, the indentations and/or protrusions can align and maintain a patient's limb 30, receive medical equipment, etc. In another aspect, the plate 42 and the center 46 can have indicia, either printed thereon and/or molded therein, to support a medical procedure. Furthermore, the plate 42 can have a planar inner surface 54 to face the image intensifier 14. In one aspect, the inner surface 54 of the plate 42 can contact the exterior facing surface of the image intensifier 14 for additional support.

In one aspect, the cap 10, the plate 42 and the center 46 can be sized larger than the image intensifier 14; and a perimeter of the center 46 of the plate 42 of the cap 10 can extend beyond a perimeter of the image intensifier 14. Thus, a useful working surface over the image intensifier 14 can be extended. In another aspect, the cap 10, the plate 42 and the center 46 can be sized and shaped to substantially match and/or cover the image intensifier 14. Thus, the cap 10 can resist interference with the operation of the medical imager 18. In another aspect, the shape of the cap 10 and the plate 42 can match a shape of the image intensifier 14. Thus, the cap 10, the plate 42 and the center 46 can be circular, rectangular, square, etc.

In another aspect, the cap 10, the plate 42 and the center 46 can be rigid and can be self-supporting to resist bearing against the image intensifier 14. The plate 42 and the center 46 can have a constant thickness of 1 inch in one aspect; less than one inch in another aspect, less than VS inch in another aspect; and substantially ¼ inch in another aspect. A thicker cap 10 and plate 42, of 1 inch for example, can make the cap 10 easier to handle and see. A thinner cap 10 and plate 42 of less than ½ inch or substantially ¼ inch, can make the cap 10 lighter and can resist interference with the imaging system. In another aspect, the cap 10, the plate 42 and/or the center 46 can be at least translucent and colored so that the image intensifier 14 can be viewed through the cap 10, the plate 42 and the center 46, and so that the cap 10, the plate 42 and the center 46 can be distinguished from the image intensifier 14. In one aspect, at least the plate 42 can be translucent with a fluorescent color to aid in visibility. In one aspect, the plate 42 can be formed of acrylic. It is believed that a plate 42 of ¼ inch thick acrylic is sufficient to resist or prevent inadvertent puncture by surgical tools 34, such as a surgical drill, through the plate 42 and into the image intensifier 18. In one aspect, the plate 42 can be a solid and continuous sheet of material spanning across an entire surface of the image intensifier 14 for protection and visibility.

The cap 10 can also comprise a retainer 62 to maintain the cap 10 on the image intensifier 14. The retainer 62 can be carried by the plate 42 and/or the image intensifier 14. In one aspect, the retainer 62 can engage the image intensifier 14 to retain the plate 42 on the image intensifier 14.

In one aspect, the retainer 62 can comprise an annular band 66 or ring circumscribing the plate 42. The annular band 66 surrounding the perimeter of the plate 42 can protect the perimeter edge of the plate 42. An interior channel 70 can be formed in an inner surface of the annular band 66 to receive a perimeter edge of the plate 42. In one aspect, the channel 70 can have a bottom, at least one lateral side, and an opposite open side. The at least one lateral side can define step or flange, and the perimeter of the plate 42 can abut to the step or flange. In another aspect, the channel 70 can have a bottom and opposing lateral sides. In one aspect, the plate 42 can be retained in the channel 70 of the band 66 by the force of friction with the channel 70 and the plate 42 sized to form a press-fit or interference-fit. In another aspect, the plate 42 can be retained in the channel 70 with a fastener, such as screws or an adhesive.

At least a portion of the band 66, such as an array of tabs 78, can extend below and beyond the inner surface 54 of the plate 42 and towards and alongside the image intensifier 14. The tabs 78 can extend from the annular band 66 perpendicular to the plate 42. An array of apertures 82 can extend through the band 66, such as being located through the array of tabs 78. An array of fasteners 86 can extend through the array of apertures 82 to engage the image intensifier 14 and secure the band 66, and thus the plate 42, to the image intensifier 14. As such, the apertures 82 and the fasteners 86 can be off-set with respect to the channel 70 and the plate 42. Thus, the array of fasteners 86 can grasp a perimeter of the image intensifier 14. The band 66 and the fasteners 86 can positively secure the cap 10 to the image intensifier 14 such that the cap 10 can be retained on the image intensifier 14 even with the c-arm 22 with the cap 10 underneath and pendent from the image intensifier 14.

In one aspect, a break 90 can be formed in, and extend radially through, the annular band 66, and defining ends of the annular band 66. The break 90 can allow the annular band 66 to expand to accept the plate 42 into the channel 70, and to contract to grip the plate 42 as described above. A fastener 94 can be located at the break 90 and between the ends of the annular band 66 to secure the ends of the annular band 66 together to resist separation of the ends of the annular band 66. In addition, the fastener 94 can be threaded to advance and refract the ends of the band 66, and to expand and contract the band 66. In one aspect, the band 66 can be formed of plastic and can be formed by injection molding.

In another aspect, the annular band 66 can be segmented into a series of arcuate segments 98 connected together in series to form the band 66. It can be easier to assemble multiple segments 98 around the plate 42. In addition, the smaller arcuate segments 98 can be formed, such as by molding, in smaller, less expensive molds and presses. The segments 98 can be coupled to proximal segments by fasteners, as described above.

The cap 10, the plate 42 and the band 66 can have the same shape as the exterior surface of the image intensifier 14. In one aspect, the cap 10, the plate 42 and the band 66 can be circular to match a circular image intensifier in another aspect, the plate 42 and the band 66 can be square to match a square image intensifier. In another aspect, the plate 42 and the band 66 can be rectangular to match a rectangular image intensifier.

In one aspect, the cap 10 can be selectively coupled to, and/or disposed on, the image intensifier 14. Thus, the cap 10 can be positioned over the image intensifier 14 when needed to protect the image intensifier 14, and removed when not needed to reduce interference with the medical imager 18. The cap 10 can have at least two positions: namely 1) an installed position, and 2) a removed position. In the installed position, the cap 10 is placed atop and over the image intensifier 14. In one aspect, the cap 10 can be positively secured to the image intensifier 14 with a fastener 86. In the removed position, the cap 10 is removed from the image intensifier 14.

Figure 7:
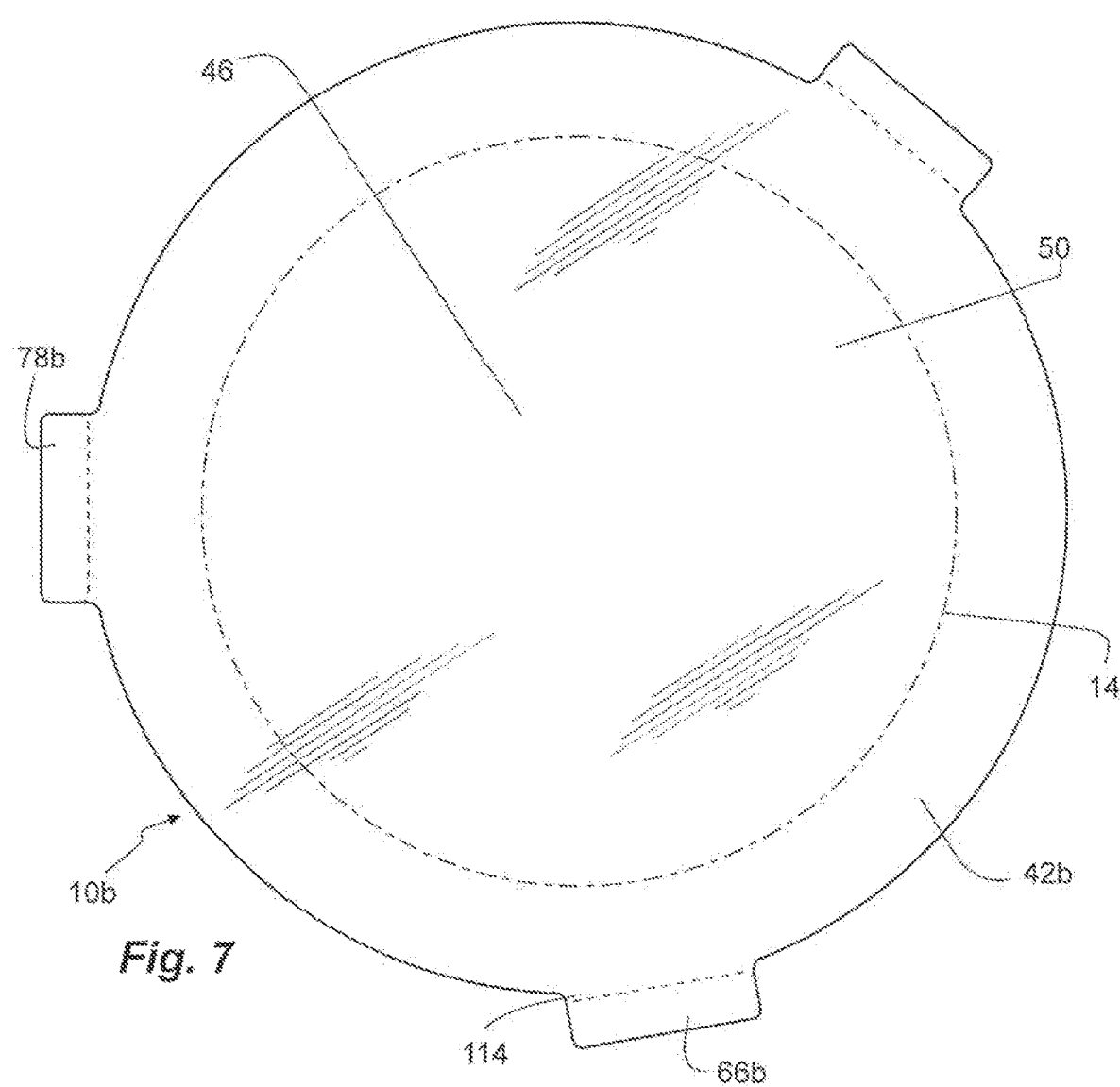
FIG. 7 is a top view of another cap shown covering an image intensifier of a medical imaging device in accordance with another embodiment of the invention.
Figure 8:
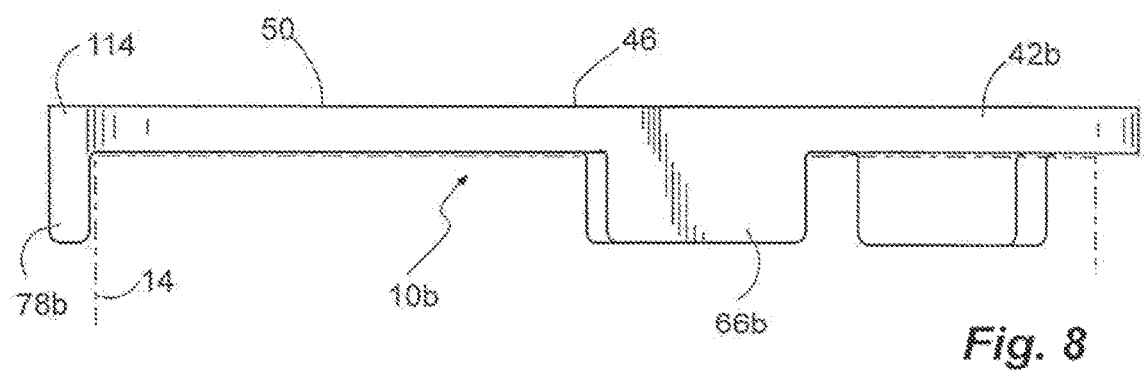
FIG. 8 is a side view of the cap of FIG. 7.
Figure 9:
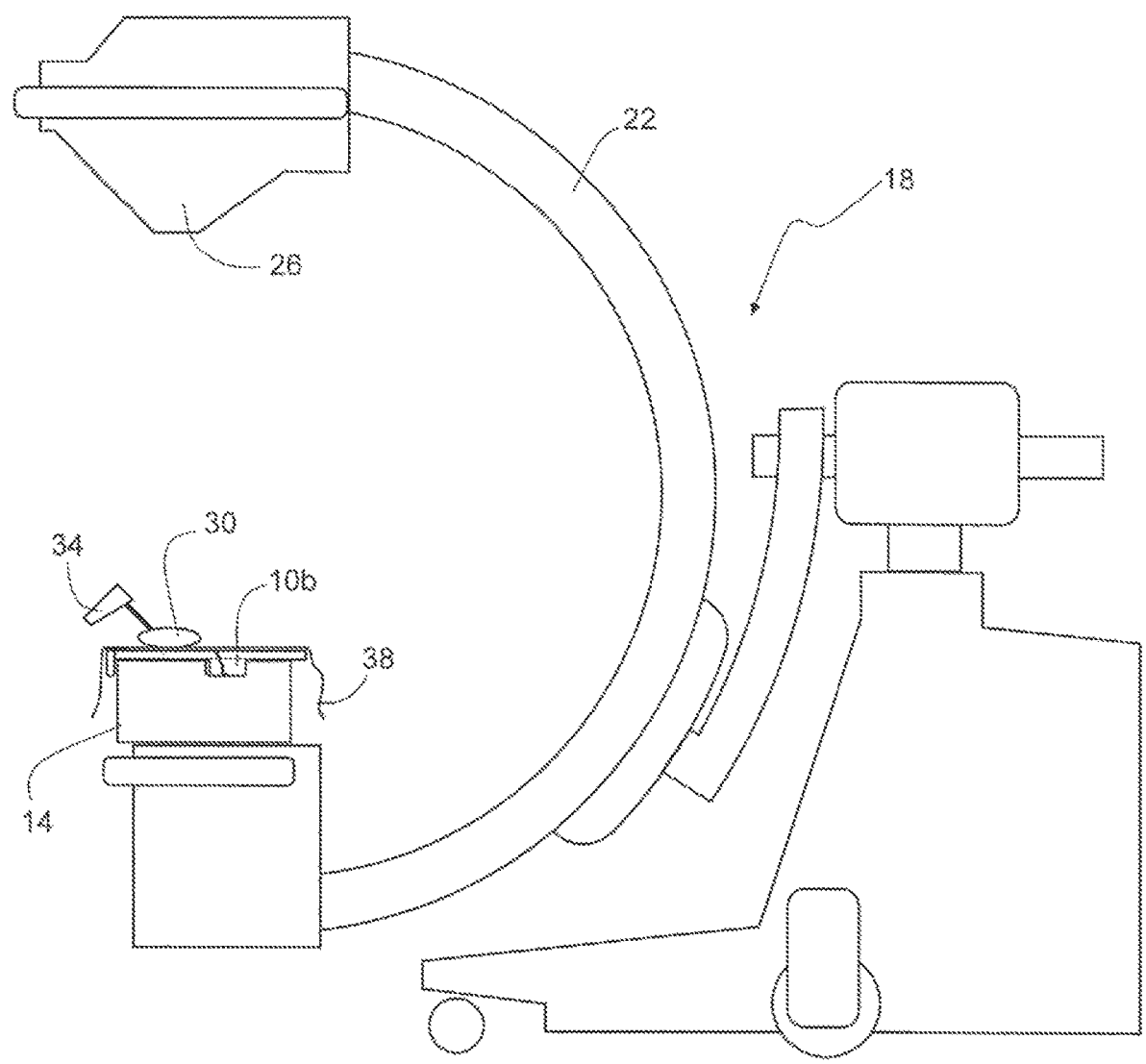
FIG. 9 is a schematic view of the cap of FIG. 7 covering the image intensifier of the c-arm medical imaging device and in use during a medical procedure in accordance with another embodiment of the invention.

Referring to FIGS. 7-9, another cap 10b is shown that is similar in many respects to the cap 10 described above, and which description is incorporated herein by reference. In one aspect, the cap 10b can be retained on the image intensifier 14 by gravity. For example, the c-arm 22 can be vertically oriented while the exterior surface of the image intensifier 14 can be oriented substantially horizontally and facing upwardly and with the cap 10b and the plate 42b positioned thereon. In addition, the cap 10b can also have a retainer 62b carried by the plate 42b and retaining the plate 42b on the image intensifier 14. The retainer 62b can comprise an array of tabs 78b arrayed around a perimeter of the center 46 of the plate 42b and extending substantially perpendicularly to the planar center 46. Thus, the tabs 78b can be arrayed around the image intensifier 14 to maintain the plate 42b on the image intensifier 14, and to resist lateral movement of the plate 42b. In one aspect, the center 46 of the plate 42b is circular and the tabs 78b comprise at least three tabs to accommodate a circular image intensifier 14. In another aspect, the center 46 and the tabs 78b can be integral and formed together from a single sheet of material with bends 114 between the center 46 and the tabs 78b. The integral plate 42b and tabs 78b can reduce part count and simplify the design. In another aspect, the tabs can be glued to the perimeter of the plate. In another aspect, the tabs can be screwed to the perimeter of the plate. In another aspect, tabs can be secured to the perimeter edge of the plate. The tabs can have holes to receive thumb screws to secure the plate and the cap to the image intensifier.

Figure 10:
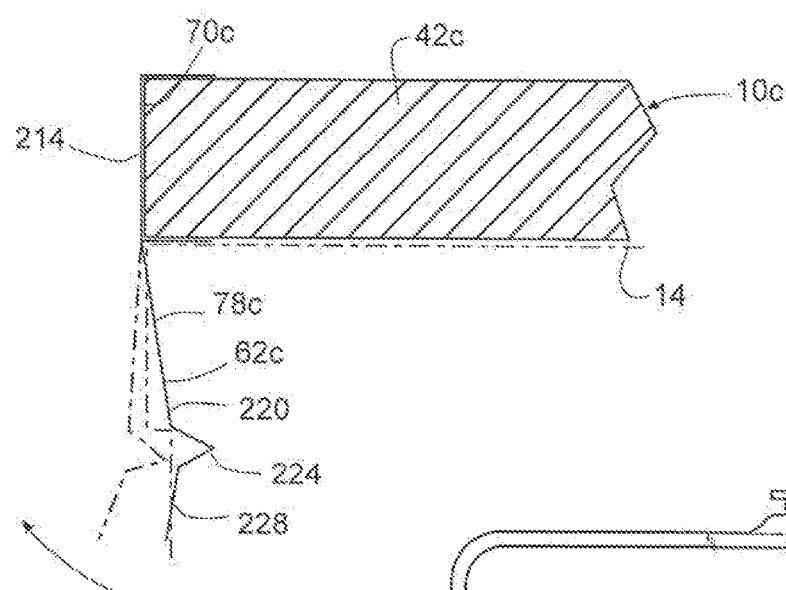
FIG. 10 is a partial cross-sectional side view of another cap shown covering an image intensifier of a medical imaging device in accordance with another embodiment of the invention.

Referring to FIG. 10, another cap 10c is shown that is similar in many respects to the caps 10 and 10b described above, and which descriptions are incorporated herein by reference. In one aspect, the plate 42c can be planar and the retainer 62c can comprise clips 78c arrayed around a perimeter of the center 46 of the plate 42c. The clips 78c can extend transvers to the planar center 46 of the plate 42c. The clips 78c can be flexible and resilient to maintain the plate 42c on the image intensifier 14. The clips 78c can be separate and distinct from the center 46 of me plate 42c. In one aspect, the dips 78c can be formed of metal, and can form leaf springs.

In one aspect, the clips 78c can have a block C-shape 214 forming a channel 70c to receive the plate 42c therein. The channel 70c can have a profile that matches a profile of the plate 42c. The channel 70c can be flexible and resilient, such as a spring, with a distance between opposite sides of the channel 70c less than a thickness of the plate 42c to expand in order to receive the plate 42c and contract to grip the plate 42c. In addition, the clips 78c can have a finger 220 extending from the channel 70c and the block C-shape 214 to engage the image intensifier 14. The clips 78c can have a bend to form a protrusion 224 to engage a corresponding indentation or edge of the image intensifier 14. The finger 220 can be flexible and resilient, such as a leaf spring, to bias the finger 220 inwardly towards the image intensifier, and to bias the protrusion 224 into the indentation or edge of me image intensifier 14. The finger 220 can have a leading edge 228 that flares outwardly so that a width or diameter of the leading edges of the fingers 220 is greater than a side or diameter of the image intensifier 14. Thus, the plate 42c, with an array of clips 78c circumscribing the plate 42c, can be placed onto me image intensifier 14 with the leading edges 228 of the fingers 220 contacting the image intensifier 14, pressed towards the image intensifier 14 to cause the fingers 220 to separate and flex outwardly and the protrusions 224 sliding along the image intensifier 14, until the plate 42c contacts and image intensifier 14 and/or the protrusions 224 of the fingers 220 mate with the corresponding indentations or edges of me image intensifier 14 to secure the plate 42c to the image intensifier 14. The use of clips 78c can allow the cap 10c and the plate 42c to be thinner and lighter weight. In addition, the dips 78c can allow the cap 10c and the plate 42c to be positively secured to the image intensifier 14 and hold the cap 10c and plate 42c on the image intensifier 14 if a technician flips the c-arm 22 upright. The cap 10c and the plate 42c can be removed by using force to overcome the clips 78c and/or bending the clips 78c outwardly. In one aspect, the cap 10c and the plate 42c can have three clips.

Figure 11:
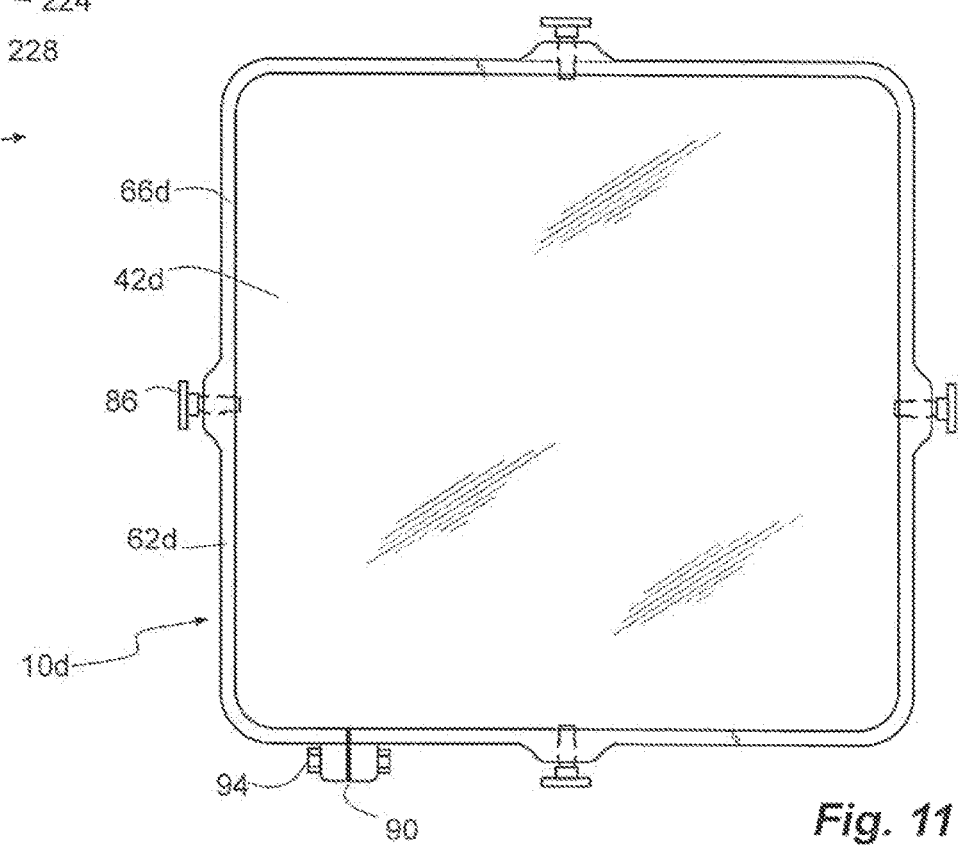
FIG. 11 is a top view of another cap for covering an image intensifier in accordance with another embodiment of the invention.

Referring to FIG. 11, another cap 10d is shown that is similar in many respects to the caps 10, 10b and 10c described above, and which descriptions are incorporated herein by reference. The cap 10d, the plate 42d, the retainer 62d and the band 66d can be rectangular, such as a square.

Figure 12:
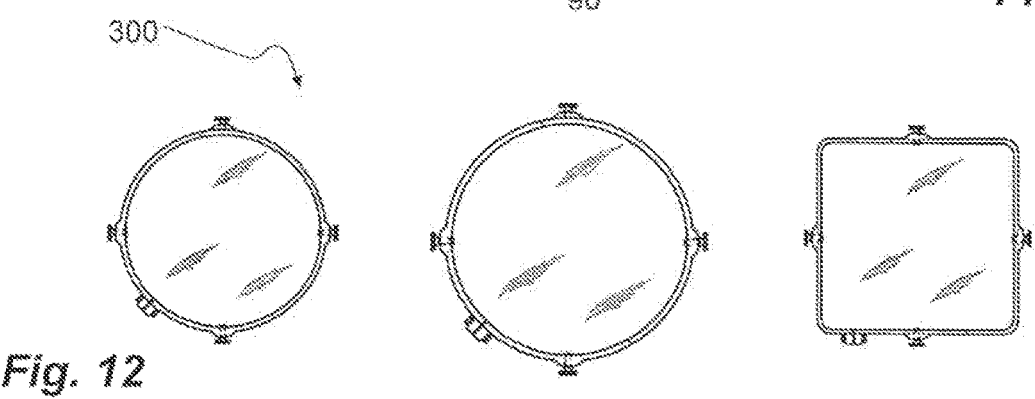
FIG. 12 is a schematic view of a cap system in accordance with another embodiment of the invention.

Referring to FIG. 12, one or more of the caps described above can be part of a cap system 300 comprising at least two caps with different sizes or shapes or both to fit different image intensifiers.

A method for protecting the image intensifier 14 of the medical imager 18 with a cap as described above (cap 10 by way of example), and for using the caps described above, can comprise:
   vertically orienting the c-arm 22 with the image intensifier 14 oriented substantially horizontally and facing substantially upwardly;
   selectively positioning the cap 10 on the image intensifier 14 with the center 46 of the cap 10 covering the image intensifier 14;
   locating a patient's limb 30 on/over the center 46 of the cap 10 and performing a medical procedure with the limb 30 supported by the
   c-arm 22 and the image intensifier 22 protected by the cap 10; and selectively removing the cap from the image intensifier.

Various aspects of x-ray transparent medical tables are disclosed in U.S. Pat. No. 6,898,810, which is hereby incorporated herein by reference. The cap, and the center and the tabs, can be formed from a sheet of acrylic, such as Plexiglas®.

As used in this specification and the appended claims, the singular forms "a," "an" and "the" include plural referents unless the context clearly dictates otherwise. Thus, for example, reference to "a layer" includes a plurality of such layers.

In this disclosure, "comprises," "comprising," "containing" and "having" and the like can have the meaning ascribed to them in U.S. Patent law and can mean "includes," "including," and the like, and are generally interpreted to be open ended terms. The terms "consisting of" or "consists of" are closed terms, and include only the components, structures, steps, or the like specifically listed in conjunction with such terms, as well as that which is in accordance with U.S. Patent law. "Consisting essentially of" or "consists essentially of" have the meaning generally ascribed to them by U.S. Patent law. In particular, such terms are generally closed terms, with the exception of allowing inclusion of additional items, materials, components, steps, or elements, that do not materially affect the basic and novel characteristics or function of the item(s) used in connection therewith. For example, trace elements present in a composition, but not affecting the composition's nature or characteristics would be permissible if present under the "consisting essentially of" language, even though not expressly recited in a list of items following such terminology. When using an open ended term in the specification, like "composing" or "including," it is understood that direct support should be afforded also to "consisting essentially of" language as well as "consisting of" language as if stated explicitly and vice versa.

The terms "first," "second," "third," "fourth," and the like in the description and in the claims, if any, are used for distinguishing between similar elements and not necessarily for describing a particular sequential or chronological order. It is to be understood that the terms so used are interchangeable under appropriate circumstances such that the embodiments described herein are, for example, capable of operation in sequences other than those illustrated or otherwise described herein. Similarly, if a method is described herein as comprising a series of steps, the order of such steps as presented herein is not necessarily the only order in which such steps may be performed, and certain of the stated steps may possibly be omitted and/or certain other steps not described herein may possibly be added to the method.

The terms "left," "right," "front," "back," "top," "bottom," "over," "under," and the like in the description and in the claims, if any, are used for descriptive purposes and not necessarily for describing permanent relative positions. It is to be understood that the terms so used are interchangeable under appropriate circumstances such that the embodiments described herein are, for example, capable of operation in other orientations than those illustrated or otherwise described herein.

The term "coupled," as used herein, is defined as directly or indirectly connected in an electrical or nonelectrical manner. Objects described herein as being "adjacent to" each other may be in physical contact with each other, in close proximity to each other, or in the same general region or area as each other, as appropriate for the context in which the phrase is used. Occurrences of the phrase "in one embodiment," or "in one aspect," herein do not necessarily all refer to the same embodiment or aspect.

As used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result. For example, a composition that is "substantially free of" particles would either completely lack particles, or so nearly completely lack particles that the effect would be the same as if it completely lacked particles, in other words, a composition that is "substantially free of" an ingredient or element may still actually contain such item as long as there is no measurable effect thereof.

As used herein, "adjacent" refers to the proximity of two structures or elements. Particularly, elements that are identified as being "adjacent" may be either abutting or connected. Such elements may also be near or close to each other without necessarily contacting each other. The exact degree of proximity may in some cases depend on the specific context.

As used herein, the term "about" is used to provide flexibility to a numerical range endpoint by providing that a given value may be "a little above" or "a little below" the endpoint. It is understood that express support is intended for exact numerical values in this specification, even when the term "about" is used in connection therewith.

The terms "interference fit" and "friction fit" and "press-fit" are terms of art used interchangeably herein to refer to deliberately causing, increasing and/or using friction to deliberately resist movement. An interference fit or friction fit is different than and great than the existence of friction. While friction may exist between any two surfaces, is often desirable to do ail one can to reduce this friction. An interference fit or friction fit can be distinguished from naturally occurring friction by being actually deliberately caused and increased. An interference fit can be created by dimensioning engaging parts so that their surfaces tightly bear against one another. A friction fit can be created by surface roughness that is rougher.

The term "ferromagnetic" is used herein to refer to a material or element that has magnetic properties and/or an ability to magnetically couple, either by being magnetic, or being magnetically attracted to a magnet (such as by containing iron) such that one ferromagnetic material or element is magnetically attracted to another ferromagnetic material or element. Thus, a ferromagnetic button is a magnet or is magnetic, such as a permanent magnet, or is attracted to magnets, such as by containing iron.

Furthermore, the described features, structures, or characteristics may be combined in any suitable manner in one or more examples. In the description, numerous specific details are provided, such as examples of lengths, widths, shapes, etc., to provide a thorough understanding of the technology being described. One skilled in the relevant art will recognize, however, that the invention can be practiced without one or more of the specific details, or with other methods, components, materials etc. In other instances, well-known structures, materials, or operations are not shown or described in detail to avoid obscuring aspects of the invention.

While the foregoing examples are illustrative of the principles of the invention in one or more particular applications, it will be apparent to those of ordinary skill in the art that numerous modifications in form, usage and details of implementation can be made without the exercise of inventive faculty, and without departing from the principles and concepts described herein. Accordingly, it is not intended that the invention be limited, except as by the claims set forth below.

It is to be understood that the examples set forth herein are not limited to the particular structures, process steps, or materials disclosed, but are extended to equivalents thereof as would be recognized by those ordinarily skilled in the relevant arts. It should also be understood that terminology employed herein is used for the purpose of describing particular examples only and is not intended to be limiting.

Furthermore, the described features, structures, or characteristics may be combined in any suitable manner in one or more examples. In the description, numerous specific details are provided, such as examples of lengths, widths, shapes, etc., to provide a thorough understanding of the technology being described. One skilled in the relevant art will recognize, however, that the invention can be practiced without one or more of the specific details, or with other methods, components, materials, etc. in other instances, well-known structures, materials, or operations are not shown or described in detail to avoid obscuring aspects of the invention.

While the foregoing examples are illustrative of the principles of the invention in one or more particular applications, it will be apparent to those of ordinary skill in the art that numerous modifications in form, usage and details of implementation can be made without the exercise of inventive faculty, and without departing from the principles and concepts described herein. Accordingly, it is not intended that the invention be limited, except as by the claims set forth below.

What is claimed is:

1. A cap configured to protect an image intensifier of a c-arm medical imaging device, the cap comprising:
   a plate sized and shaped to cover an exterior facing surface of the image intensifier;
   the plate being transparent to x-rays;
   the plate having a planar center with a planar outer surface and a planar inner surface configured to face the image intensifier;
   a retainer carried by the plate and configured to engage the image intensifier to retain the plate on the image intensifier; and
   the retainer further comprising tabs arrayed around a perimeter of the center of the plate and extending substantially perpendicularly to the planar center and configured to be arrayed around the image intensifier to maintain the plate on the image intensifier.

2. The cap in accordance with claim 1, wherein the center of the plate is circular and the tabs comprise at least three tabs.

3. The cap in accordance with claim 1, wherein the center and the tabs are integral and formed together from a single sheet of material with bends between the center and the tabs.

4. The cap in accordance with claim 1, wherein the retainer further comprises:
   an array of apertures located in the tabs; and
   an array of fasteners extending through the array of apertures and configured to engage the image intensifier to secure the plate to the image intensifier.

5. The cap in accordance with claim 1, wherein the retainer further comprises:
   an annular band circumscribing the plate; and
   the tabs extending from the annular band perpendicular to the plate.

6. The cap in accordance with claim 1, wherein the plate is translucent and colored to view the image intensifier through the plate while distinguishing the plate from the image intensifier.

7. A c-arm medical imaging device comprising the cap in accordance with claim 1, and further comprising:
   an image intensifier and an opposing x-ray source directed at the image intensifier; and
   the cap being selectively coupled to and disposed over the image intensifier.

8. The cap in accordance with claim 1, wherein the inner surface of the plate contacts the image intensifier when the cap is coupled to the image intensifier.

9. A cap configured to protect an image intensifier of a c-arm medical imaging device, the cap comprising:
   a plate sized and shaped to cover an exterior facing surface of the image intensifier;
   the plate being transparent to x-rays;
   the plate having a planar center with a planar outer surface and a planar inner surface configured to face the image intensifier; and
   a retainer carried by the plate and configured to engage the image intensifier to retain the plate on the image intensifier, the retainer comprising:
   an annular band circumscribing the plate;
   an array of apertures through the band; and
   an array of fasteners extending through the array of apertures and configured to engage the image intensifier to secure the band and the plate to the image intensifier.

10. The cap in accordance with claim 9, wherein the annular band comprises a series of arcuate segments fastened together.

11. The cap in accordance with claim 9, wherein the retainer further comprises:
    a channel in an inner surface of the annular band receiving a perimeter edge of the plate;
    an array of tabs extending from the annular band perpendicular to the plate;
    the array of apertures being located in the array of tabs, and off-set with respect to the channel and the plate.

12. The cap in accordance with claim 9, wherein the retainer further comprises:
    a break in the annular band allowing the annular band to expand and contract, and defining ends of the annular band; and
    a fastener at the break and between the ends of the annular band and securing the ends of the annular band together to resist separation of the ends of the annular band.

13. The cap in accordance with claim 9, wherein the plate is translucent and colored to view the image intensifier through the plate while distinguishing the plate from the image intensifier.

14. A c-arm medical imaging device comprising the cap in accordance with claim 9, and further comprising:
    an image intensifier and an opposing x-ray source directed at the image intensifier; and
    the cap being selectively coupled to and disposed over the image intensifier.

15. The cap in accordance with claim 14, wherein the inner surface of the plate contacts the image intensifier when the cap is coupled to the image intensifier.

16. A cap configured to protect an image intensifier of a c-arm medical imaging device, the cap comprising:
    a plate sized and shaped to cover an exterior facing surface of the image intensifier;
    the plate being transparent to x-rays;
    the plate having a planar center with a planar outer surface and a planar inner surface configured to face the image intensifier;
    a retainer carried by the plate and configured to engage the image intensifier to retain the plate on the image intensifier; and
    the plate being at least translucent to view the image intensifier through the plate and being colored to distinguish the plate from the image intensifier.

17. The cap in accordance with claim 16, wherein the retainer further comprises:
    tabs arrayed around a perimeter of the center of the plate and extending substantially perpendicularly to the planar center and configured to be arrayed around the image intensifier to maintain the plate on the image intensifier.

18. The cap in accordance with claim 16, wherein the retainer further comprises:
    an annular band circumscribing the plate;
    an array of apertures through the band; and
    an array of fasteners extending through the array of apertures and configured to engage the image intensifier to secure the band and the plate to the image intensifier.

19. A c-arm medical imaging device comprising the cap in accordance with claim 16, and further comprising:

an image intensifier and an opposing x-ray source directed at the image intensifier;

the cap being selectively coupled to and disposed over the image intensifier; and the inner surface of the plate contacts the image intensifier when the cap is coupled to the image intensifier.

\* \* \* \* \*